US009283266B2

(12) United States Patent
Suckow et al.

(10) Patent No.: US 9,283,266 B2
(45) Date of Patent: Mar. 15, 2016

(54) METASTASIS INHIBITION PREPARATIONS AND METHODS

(75) Inventors: Mark A. Suckow, South Granger, IN (US); William R. Wolter, South Bend, IN (US); Valerie Sailes, Mishawaka, IN (US)

(73) Assignee: UNIVERSITY OF NOTRE DAME, Notre Dame, IN (US)

(*) Notice: Subject to any disclaimer, the term of this patent is extended or adjusted under 35 U.S.C. 154(b) by 1809 days.

(21) Appl. No.: 12/039,166

(22) Filed: Feb. 28, 2008

(65) Prior Publication Data

US 2009/0220461 A1 Sep. 3, 2009

(51) Int. Cl.
A61K 39/00 (2006.01)
A61K 35/55 (2015.01)
A61K 35/00 (2006.01)

(52) U.S. Cl.
CPC .............. *A61K 39/0011* (2013.01); *A61K 35/55* (2013.01); *A61K 35/00* (2013.01); *A61K 2039/5152* (2013.01); *A61K 2039/55566* (2013.01)

(58) Field of Classification Search
CPC ........... A61K 39/0011; A61K 2300/00; A61K 2039/5152; A61K 38/00; A61K 39/39558; A61K 39/3955; A61K 45/06; A61K 47/48569; A61K 51/1045; A61K 2039/5156; A61K 39/00; A61K 47/48423; A61K 47/48561; A61K 2039/5158; A61K 2039/522
See application file for complete search history.

(56) References Cited

U.S. PATENT DOCUMENTS

| | | | |
|---|---|---|---|
| 2,172,903 A | 9/1939 | Charping | |
| 3,346,401 A | 10/1967 | Barat et al. | |
| 3,562,820 A | 2/1971 | Braun | |
| 3,810,473 A | 5/1974 | Cruz, Jr. et al. | |
| 4,502,159 A | 3/1985 | Woodroof et al. | |
| 4,578,067 A | 3/1986 | Cruz, Jr. et al. | |
| 4,902,508 A | 2/1990 | Badylak et al. | |
| 4,956,178 A | 9/1990 | Badylak et al. | |
| 5,028,695 A | 7/1991 | Eckmayer et al. | |
| 5,273,745 A * | 12/1993 | Schirrmacher | 424/277.1 |
| 5,275,826 A | 1/1994 | Badylak et al. | |
| 5,281,422 A | 1/1994 | Badylak et al. | |
| 5,336,616 A | 8/1994 | Livesey et al. | |
| 5,352,463 A | 10/1994 | Badylak et al. | |
| 5,372,821 A | 12/1994 | Badylak et al. | |
| 5,437,287 A | 8/1995 | Phillips et al. | |
| 5,460,962 A | 10/1995 | Kemp | |
| 5,480,424 A | 1/1996 | Cox | |
| 5,507,810 A | 4/1996 | Prewett et al. | |
| 5,554,389 A | 9/1996 | Badylak et al. | |
| 5,645,860 A | 7/1997 | Knapp et al. | |
| 5,695,998 A | 12/1997 | Badylak et al. | |
| 5,733,337 A | 3/1998 | Carr, Jr. et al. | |
| 5,782,914 A | 7/1998 | Schankereli | |
| 5,837,269 A | 11/1998 | Danes et al. | |
| 6,120,991 A | 9/2000 | Carter et al. | |
| 6,156,305 A | 12/2000 | Brauker et al. | |
| 6,206,931 B1 | 3/2001 | Cook et al. | |
| 6,207,147 B1 | 3/2001 | Hiserodt et al. | |
| 6,218,166 B1 | 4/2001 | Ravindranath et al. | |
| 6,264,992 B1 | 7/2001 | Voytik-Harbin et al. | |
| 6,277,368 B1 | 8/2001 | Hiserodt et al. | |
| 6,403,104 B1 | 6/2002 | Berd et al. | |
| 6,406,689 B1 | 6/2002 | Falkenberg et al. | |
| 6,451,971 B1 | 9/2002 | Akiyama et al. | |
| 6,548,066 B1 | 4/2003 | Michaeli et al. | |
| 6,699,483 B1 | 3/2004 | Dalgleish et al. | |
| 7,015,205 B1 | 3/2006 | Wallack et al. | |
| 7,090,853 B2 | 8/2006 | Kapp et al. | |
| 7,175,652 B2 | 2/2007 | Cook et al. | |
| 7,247,310 B1 * | 7/2007 | Ohno et al. | 424/277.1 |
| 7,550,004 B2 | 6/2009 | Bahler et al. | |
| 2001/0006631 A1 | 7/2001 | Hiserodt et al. | |
| 2002/0001595 A1 | 1/2002 | Sonntag et al. | |
| 2003/0014126 A1 | 1/2003 | Patel et al. | |
| 2004/0013712 A1 | 1/2004 | Parma | |
| 2006/0099675 A1 | 5/2006 | Benard | |
| 2006/0265053 A1 | 11/2006 | Hunt | |
| 2007/0128174 A1 | 6/2007 | Kleinsek et al. | |
| 2008/0107665 A1 | 5/2008 | Suckow et al. | |
| 2008/0160049 A1 | 7/2008 | Suckow et al. | |
| 2008/0260800 A1 | 10/2008 | Suckow et al. | |

(Continued)

FOREIGN PATENT DOCUMENTS

| | | |
|---|---|---|
| WO | WO97/36495 | 10/1997 |
| WO | WO03/100034 | 12/2003 |

(Continued)

OTHER PUBLICATIONS

Kobayashi et al. J Int Med 8(1) 2004. pp. 97-101.*
Baars A, Claessen AME, van den Eertwegh AJM, Gall HE, Stam AGM, Meijer S, Giaccone G, Meijer CJLM, Scheper RJ, Wagstaff J, Vermorken JB, Pinedo HM (2000) Skin tests predict survival after autologous tumor cell vaccination in metastatic melanoma: experience in 81 patients. Ann Oncol 11:965-970.
Berd D, Maguire HC, Jr, McCue P, Mastrangelo MJ (1990) Treatment of metastatic melanoma with an autologous tumor-cell vaccine: clinical and immunologic results in 64 patients. J Clin Oncol 8:1858-1867.
Burch PA, Breen JK, Buckner JC, Gastineau DA, Kaur JA, Laus RL, Padley DJ, Peshwa MV, Pitot HC, Richarson RL, Smits BJ, Sopapan P, Strang G, Valone FH, Vuk-Pavlovic S (2000) Priming tissue-specific cellular immunity in a phase I trial of autologous dendritic cells for prostate cancer. Clin Cancer Res 6:2175-2182.

(Continued)

*Primary Examiner* — Blaine Lankford
(74) *Attorney, Agent, or Firm* — Husch Blackwell LLP; Denise L. Mayfield

(57) ABSTRACT

Disclosed are compositions and pharmaceutical preparations suitable for inhibiting metastasis of a malignant cancer in an animal. Methods for inhibiting and/or eliminating metastasis in an animal are also provided. In some embodiments, the preparations and compositions comprise a whole cell tumor preparation comprising tumor tissue cells and tumor connective tissue stroma. The disclosure also provides methods for preparing the preparations and pharmaceutical preparations. Inhibition of metastasis of malignant prostate cancer to the lung is shown in vivo.

9 Claims, 3 Drawing Sheets

(56) References Cited

U.S. PATENT DOCUMENTS

| | | |
|---|---|---|
| 2009/0220461 A1 | 9/2009 | Suckow et al. |
| 2009/0248144 A1 | 10/2009 | Bahler et al. |
| 2010/0124573 A1* | 5/2010 | Naughton et al. ............ 424/520 |

FOREIGN PATENT DOCUMENTS

| | | |
|---|---|---|
| WO | WO2008/051852 | 5/2008 |
| WO | WO2008/094276 | 8/2008 |
| WO | WO2008/112344 | 9/2008 |
| WO | WO2009/108656 | 9/2009 |

OTHER PUBLICATIONS

Burch PA, Croghan GA, Gastineau DA, Jones LA, Kaur JS, Kylstra JW, Richardson RL, Valone FH, Vuk-Pavlovic S (2004) Immunotherapy (APC8015, Provenge) targeting prostatic acid phosphatase can induce durable remission of metastatic androgen-independent prostate cancer: a Phase 2 trial. Prostate 60:197-204.

Corman JM, Secarz EE, Nanda NK (1998) Recognition of prostate-specific antigenic peptide determinants by human CD4 and CD8 T cells. Clin Exp Immunol 114:166-172.

Correale P, Walmsley K, Nieroda C, Zaremba S, Zhu M, Schlom J, Tsang KY (1997) In vitro generation of human cytotoxic T lymphocytes specific for peptides derived from prostate-specific antigen. J Natl Cancer Inst USA 89:293-300.

Dillman RO, Nayak SK, Barth NM, DeLeon C, Schwartzberg LS, Spitler LE, Church C, O'Connor AA, Beutel LD (1998) Clinical experience with autologous tumor cell lines for patient-specific vaccine therapy in metastatic melanoma. Cancer Biother Radiopharm 13:165-173.

Edwards BK, Brown ML, Wingo PA, Howe HL, Ward E, Ries LA, Schrag D, Jamison PM, Jemal A, Wu XC, Friedman C, Harlan L, Warren J, Anderson RN, Pickle LW (2005) Annual report to the nation on the status of cancer, 1975-2002, featuring population-based trends in cancer treatment. J Natl Cancer Inst 97:1407-1427.

Fong L, Brockstedt D, Benike C, Breen JK, Strang G, Ruegg CL, Engleman EG (2001) Dendritic cell-based xenoantigen vaccination for prostate cancer immunotherapy. J Immunol 167:7150-7156.

Fuessel S, Meye A, Schmitz M, Zastrow S, Linná C, Richter K, Lobel B, Hakenberg OW, Hoelig K, Rieber EP, Wirth MP (2006) Vaccination with hormone-refractory prostate cancer patients with peptide cocktail-loaded dendritic cells: results of a phase I clinical trial. Prostate 66:811-821.

Granziero L, Krajewski 5, Farness P, Yuan L, Courtney MK, Jackson MR, Peterson PA, Vitiello A (1999) Adoptive immunotherapy prevents prostate cancer in a transgenic animal model. Eur J Immunol 29:1127-1138.

Harada M, Kobayashi K, Matsueda S, Nakagawa M, Noguchi M, Itoh K (2003) Prostate-specific antigen-derived epitopes capable of inducing cellular and humoral responses in HLA-A24+ prostate cancer patients. Prostate 57:152-159.

Hodde, Jason P., Suckow, Mark A., Wolter, William R., Hiles, Michael C. (2004) Small Intestinal Submucosa Does Not Promote PAIII Tumor Growth in Lobund-Wistar Rats. Journal of Surgical Research 120, 189-194.

Horiguchi Y, Nukaya I, Okazawa K, Kawashima I, Fikes J, Sette A, Tachibana A, Takesako K, Murai M (2002) Screening of HLA-A24-restricted epitope peptides from prostate-specific membrane antigen that induces specific antitumor cytotoxic T lymphocytes. Clin Cancer Res 8:3885-3892.

Hrouda D, Todryk SM, Perry MJ, Souberbielle BE, Kayaga J, Kirby RS, Dalgleish AG (2000) Allogeneic whole-tumour cell vaccination in the rat model of prostate cancer. BJU Int 86:742-748.

Jocham D, Richter A, Hoffinann L, Twig K, Fahlenkamp D, Zakrzewski G, Schmitt E, Danneberg T, Lehmacher W, von Wietersheim J, Doehn C (2004) Adjuvant autologous renal tumour cell vaccine and risk of tumour progression in patients with renal-cell carincoma after radical nephrectomy: phase III, randomised controlled trial. Lancet 363:594-599.

Kobayashi H, Omiya R, Sodey B, Yanai M, Oikawa K, Sato K, Kimura S, Senju S, Nishimura Y, Tateno M, Celis E (2003) Identification of naturally processed helper T-cell epitopes from prostate-specific membrane antigen using peptide-based in vitro stimulation. Clin Cancer Res 9:5386-5393.

Lu J, Celis E (2002) Recognition of prostate tumor cells by cytotoxic T lymphocytes specific for prostate-specific membrane antigen. Cancer Res 62:5807-5812.

Matsueda S, Takedatsu H, Yao A, Tanaka M, Noguchi M, Itoh K, Harada M (2005) Identification of peptide vaccine candidates for prostate cancer patients with HLS-A3 super-type alleles. Clin Cancer Res 11:6933-6943.

McNeel DG, Nguyen LD, Disis ML (2001) Identification of T helper epitopes from prostatic acid phosphatase. Cancer Res 61:5161-5167.

Michael A, Ball G, Quatan N, Wushishi F, Russell N, Whelan J, Chakraborty P, Leader D, Whelan M, Pandha H (2005) Delayed disease progression after allogeneic cell vaccination in hormone-resistant prostate cancer and correlation with immunologic variables. Clin Cancer Res 11:4469-4478.

Moody DB, Robinson JC, Ewing CM, Lazenby AJ, Isaacs WB (1994) Interleukin-2 transfected prostate cancer cells generate a local antitumor effect in vivo. Prostate 24:244-251.

Pollard M, Suckow MA (2006) Dietary prevention of hormone refractory prostate cancer in Lobund Wistar rats: a review of studies in a relevant animal model. Comp Med 56:461-467.

Pollard M, Luckert PH (1975) Transplantable, metastasizing adenocarcinomas in rats. J Natl Cancer Inst 54:643-649.

Simons JW, Mikhak B, Chang J-F, DeMarzo AM, Carducci MA, Lim M, Weber CE, Baccala AA, Goemann MA, Clift SM, Ando DG, Levitsky BI, Cohen LK, Sanda MG, Mulligan RC, Partin AW, Carter HB, Piantadosi S, Marshall FF, Nelson WG (1999) Induction of immunity to prostate cancer antigens: results of a clinical trial of vaccination with irradiated autologous prostate tumor cells engineered to secrete granulocyte-macrophage colony-stimulating factor using ex vivo gene transfer. Cancer Res 59:5160-5168.

Simons J, Nelson W, Nemunaitis J, Centeno A, Dula E, Urba W, Smith D, Marshall F, Howard C, Ando D, Small E (2002) Phase II trials of a GM-CSF genetransduced prostate cancer cell line vaccine (GVAX) in hormone refractory prostate cancer. Proc Am Soc Clin Oncol 21:729.

Small EJ, Fratesi P, Reese DM, Strang G, Laus R, Peshwa MV, Valone FH (2000) Immunotherapy of hormone-refractory prostate cancer with antigen-loaded dendritic cells. J Clin Oncol 18:3894-3903.

Small EJ, Schellhammer PF, Higano CS, Neumanaitis J, Valone F, Hershberg R (2005) Results of a placebo-controlled phase III trial of immunotherapy with APC8015 for patients with hormone refractory prostate cancer (HRPC). Proc Am Soc Clin Oncol 23(16S):4500.

Stack BH, McSwan N, Stirling JM, Hole DJ, Spilg WG, McHattie I, Elliott JA, Gillis CR, Turner MA, White RG (1982) Autologous x-irradiated tumour cells and percutaneous BCG in operable lung cancer, Thorax 37:588-593.

Suckow MA, Wolter WR, Pollard M (2005) Prevention of de novo prostate cancer by immunization with tumor-derived vaccines. Cancer Immunol Immunother 54:571576.

Vermorken JB, Claessen AME, van Tinteren H, Gall HE, Ezinga R, Meijer S, Scheper RJ, Meijer CJLM, Bloemena E, Ransom JH, Hanna MG, Jr, Pinedo HM (1999) Active specific immunotherapy for stage II and stage III human colon cancer: a randomized trial. Lancet 353:345-350.

Vieweg J, Rosenthal FM, Bannerji R, Heston WD, Fair WR, Gansbacher B, Gilboa E (1994) Immunotherapy of prostate cancer in the Dunning rat model: use of cytokine gene modified tumor vaccines. Cancer Res 54:1760-1765.

Wilson, Michael J., Sinha, Akhouri A. (1997) Human Prostate Tumor Angiogenesis in Nude Mice: Metalloprotease and Plasminogen Activator Activities During Tumor Growth and Neovascularization of Subcutaneously Injected Matrigel Impregnated With Human Prostate Tumor Cells. The Anatomical Record 249:63-73.

Xue BH, Zhang Y, Sosman JA, Peace DJ (1997) Induction of human cytotoxic T lymphocytes specific for prostate-specific antigen. Prostate 30:73-78.

Zhang S, Zeng G, Wilkes DS, Reed GE, McGarry RC, Eble JN, Cheng L (2003) Dendritic cells transfected with interleukin-12 and

(56) References Cited

OTHER PUBLICATIONS pulsed with tumor extract inhibit growth of murine prostatic carcinoma in vivo. Prostate 55:292-298.

Aguzzi et al., (2003), "Immune system and peripheral nerves in propagation of prions to CNS," *Br Med Bull.*, 2003;66:141-59.

Aguzzi et al., (2006), "Pathogenesis of prion diseases: current status and future outlook," *Microbiology*, 4:765-775.

Akhurst, (2002), "TGF-B antagonists: why suppress a tumor suppressor?" *J. Clin. Invest.*, 109:1533-1536.

Allman et al., (2001), "Xenogeneic extracellular matrix grafts elicit a TH2-restricted immune response," *Transplantation*, 71:1631-1640.

Arbel et al., (2003), "Generation of antibodies against prion protein in wild-type mice via helix 1 peptide immunization," J Neuroimmunol., 144(1-2):38-45.

Badylak et al., (1989), "Small intestinal submucosa as a large diameter vascular graft in the dog," *J. Surgical Res.*, 47:74-80.

Badylak et al., (1998), "Small intestinal submucosa: a substrate for in vitro cell growth," *J. Biomater. Sci. Polymer Edn.*, 9:863-878.

Badylak et al., (2002), "The extracellular matrix as a scaffold for tissue reconstruction," *Cell Devel. Biol.*, 13:377-383.

Badylak, (1993), "Small intestinal submucosa (SIS): a biomaterial conducive to smart tissue remodeling," *Tissue Engineering: Current Perspectives*, Bell (ed)., Birkhauser Publishers, Cambridge, MA, pp. 179-189.

Banzhoff et al., (2003), "A new MF59-adjuvanted influenza vaccine enhances the immune response in the elderly with chronic diseases: results from an immunogenicity meta-analysis," *Gerontology*, 49(3):177-84.

Barr et al., (2006), "Co-stimulatory agonists as immunological adjuvants," *Vaccine*, 24:3399-3407.

Bello-DeOcampo et al., (2004), "TGF-B/Smad signaling in prostate cancer," *Curr. Drug Targets*, 4:197-207.

Benbow, (2001), "Oasis®: an innovative alternative dressing for chronic wounds," *Brit. J. Nursing*, 10:1489-1492.

Bendani et al., (2006), "Combined vaccination with idiotype-pulsed allogeneic dendritic cells and soluble protein idiotype for multiple myeloma patients relapsing after reduced-intensity conditioning allogeneic stem cell transplantation," *Leukemia & Lymphoma*, 41:29-37.

Ben-Efraim et al., (2000), "Use of xenogenized (modified) tumor cells for treatment in experimental tumor and in human neoplasia," *Biomed & Pharmacotherapy*, 54:268-273.

Berd et al., (1997), "Autologous hapten-modified melanoma vaccine as post-surgical adjuvant after resection of nodal metastases," *J. Clin. Oncol.*, 15:2359-2370.

Bergman et al., (2003), "Long-term survival of dogs with advanced malignant melanoma after DNA vaccination with xenogeneic human tyrosinase: a phase I trial," *Clin. Cancer Res.*, 9:1284-1290.

Berraondo et al., (2007), "Eradication of large tumors in mice by a tritherapy targeting the innate, adaptive, and regulatory components of the immune system," *Cancer Res.*, 67:8847-8855.

Bissell et al., (1987), "The influence of extracellular matrix on gene expression: is structure the message?" *J. Cell Sci.*, Suppl 8:327-343.

Bodey et al., (2000), "Failure of cancer vaccines: the significant limitations of this approach to immunotherapy," *Anticancer Res.*, 20:2665-2676.

Boring et al., (1993), "Cancer Statistics," *CA Cancer Journal for Clinicians*, 43:7-26.

Brando et al., (2007), "Murine immune responses to liver-stage antigen 1 protein FMP011, a malaria vaccine candidate, delivered with adjuvant AS01B or AS02A," *Infect Immun.*, 75(2):838-45.

Brewer, (2006), "(How) do aluminium adjuvants work?" *Immunol. Lett.*, 102:10-15.

Brooks et al., (2001), "Plasma selenium level before diagnosis and the risk of prostate cancer development," *Journal of Urology*, 166:2034-2038.

Brown-Etris et al., (2002), "Part I: A new biomaterial derived from small intestine submucosa and developed into a wound-matrix device," *Wounds*, 14:150-166.

Caglar et al., (2005), "Effect of monophosphoryl lipid A on antibody response to diphtheria toxin and its subunits," *APMIS*, 113(4):256-63.

Caughey et al., (2006), "Prions and their Partners in Crime," *Nature*, 443:803-810.

Chang et al., (2000), "Antigen-Specific Cancer Immunotherapy Using a GM-CSF secreting allogeneic tumor cell-based vaccine," *Int. J. Cancer*, 86:725-730.

Charles et al., (2000), "Antitumor efficacy of tumor-antigen-encoding recombinant poxvirus immunization in dunning rate prostate cancer: implications for clinical genetic vaccine development," *World J. Urol.*, 18:136-142.

Chatterjee et al., (1994), "Idiotypic antibody immunotherapy of cancer," *Cancer Immunol. Immunother.*, 38:75-82.

Culora et al., (1996), "Aluminium and injection site reactions," *J. Clin. Pathol.*, 49:844-847.

Cunha et al., (2003), "Role of the stromal microenvironment in carcinogenesis of the prostate," *Int. J. Cancer*, 107:1-10.

de Souza Matos et al., (2000), "Immunostimulatory effects of polar glycopeptidolipids of *Mycobacterium chelonae* for inactivated rabies vaccine," *Vaccine*, 18(20):2125-31.

Degruijl et al., (1999), "Cancer vaccine strategies get bigger and bigger," *Nature Medicine*, 5:1124-1125.

Denmeade et al., (2003), "Prostate specific antigen (PSA) does not affect growth of prostate cancer cells in vitro or prostate cancer xenografts in vivo," *Prostate*, 56:45-53.

Desai et al., (2000), "Immune response with biodegradable nanospheres and alum: studies in rabbits using staphylococcal enterotoxin B-toxoid," *J Microencapsul.*, 17(2):215-25.

Dillman et al., (2001), "Short-term cell lines from breast cancer for use as autologous tumor cell vaccines in the treatment of breast cancer," *Cancer Biotherapy & Radiopharmaceuticals*, 16:205-211.

Dols et al., (2003), "Vaccination of women with metastatic breast cancer using a costimulatory gene (CD80)-modified, HLA-A2 matched allogeneic, breast cancer cell line: clinical and immunological results," *Human Gene Therapy*, 14:1117-1123.

Donnelly, (2003), "Cancer vaccine targets leukemia," *Nature Medicine*, 9:1354-1356.

Eaton et al., (2002), "Allogeneic whole-cell vaccine: a phase I/II study in men with hormone-refractory prostate cancer," *British Journal of Urology*, 89:19-26.

Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies," *Infect Immun.*, 59(9):2978-86.

Enari et al., (2001), "Scrapie prion protein accumulation by scrapie-infected neuroblastoma cells abrogated by exposure to a prion protein antibody," *Proc Natl Acad Sci U S A*, 98(16):9295-9.

Evans et al., (1999), "Vaccine therapy for cancer—fact or fiction?" *Q. J. Med.*, 92:299-307.

Ezzell, (1995), "Cancer 'vaccines': an idea whose time has come?" *J. NIH Res.*, 7:4-49.

Fernandez-Acenero et al., (2002), "Prognostic influence of tumor-associate eosinophilic infiltrate in colorectal carcinoma," *Cancer*, 88:1544-1548.

Finn et al., (2002), "Prophylactic Cancer Vaccines," *Curr. Opin. Immunol.*, 14:172-177.

Flick-Smith et al., (2002), "Mucosal or parenteral administration of microsphere-associated Bacillus anthracis protective antigen protects against anthrax infection in mice," *Infect Immun.*, 70(4):2022-8.

Forni et al., (2000), "Immunoprevention of cancer," *Cancer Res.*, 60:2571-2575.

Frost et al., (1975), "Tumor immunoprophylaxis in mice using glutaraldehyde-treated syngenic tumor cells," *Cancer Res.*, 35:2646-2650.

Fukino et al., (2004), "Combined total genome loss of heterozygosity scan of breast cancer stroma and epithelium reveals multiplicity of stromal targets," *Cancer Res.*, 64:7231-6.

Furbert-Harris et al., (2003), "Inhibition of prostate cancer cell growth by activate eosinophils," *The Prostate*, 57:165-175.

Gann et al., (1999), "Lower prostate cancer risk in men with elevated plasma lycopene levels: results of a prospective analysis," *Cancer Research*, 59:1225-1230.

(56) References Cited

OTHER PUBLICATIONS

Gann et al., (1999), "Lower prostate cancer risk in men with elevated plasma lycopene levels: results of a prospective analysis," *JAMA*, 281:1682.
Gilch et al., (2003), "Polyclonal anti-PrP auto-antibodies induced with dimeric PrP interfere efficiently with PrPSc propagation in prion-infected cells," *J Biol Chem.*, 278(20):18524-31.
Glenn et al., (2006), "Mass vaccination: solutions in the skin," *Curr. Topics Microbiol. Immunol.*, 304:247-268.
Greenlee et al., (2001), "Cancer Statistics 2001," *CA Cancer J. Clin.*, 51:15-36.
Griffith et al., (2001), "Inhibition of murine prostate tumor growth and activation of immunoregulatory cells with recombinant canarypox viruses," *J. Natl. Cancer Inst.*, 93:998-1007.
Griffiths et al., (1997), "Liposomally-encapsulated ricin toxoid vaccine delivered intratracheally elicits a good immune response and protects against a lethal pulmonary dose of ricin toxin," *Vaccine*, 15(17-18):1933-9.
Gu et al., (2002), "Substitution of porcine small intestinal submucosa for rabbit Achilles tendon, an experimental study," *Natl. Med. J. China*, 82:1279-1282 (Chinese language with English abstract).
Gulley et al., (2002), "Phase I study of a vaccine using recombinant vaccinia virus expressing PAS (rV-PSA) in patients with metastatic androgen-independent prostate cancer," *The Prostate*, 53:109-117.
Hahn et al., (2006), "Short-term dietary administration of celecoxib enhances the efficacy of tumor lysate-pulsed dendritic cell vaccines in treating murine breast cancer," *Int. J. Cancer*, 118:2220-2231.
Hanan et al., (2001), "Antiaggregating antibody raised against human PrP 106-126 recognizes pathological and normal isoforms of the whole prion protein," *Cell Mol Neurobiol.*, 21(6):693-703.
Hanan et al., (2001), "Immunomodulation of the human prion peptide 106-126 aggregation," Biochem Biophys Res Commun., 280(1):115-20.
He et al., (2003), "Inhibition of tumor growth with a vaccine based on xenogeneic homologous fibroblast growth factor receptor-1 in mice," *J. Biol. Chem.*, 24:21831-21836.
He et al., (2005), "Antigen epitope-expressing cytokines for DNA immunization," *Vaccine*, 23:1966-1972.
Hedlund et al., (2001), "Negligible adjuvant effect for antibody responses and frequent adverse events associated with IL-12 treatment in humans vaccinated with pneumococcal polysaccharide," *Vaccine*, 20(1-2):164-9.
Higgins et al., (1996), "MF59 adjuvant enhances the immunogenicity of influenza vaccine in both young and old mice," *Vaccine*, 14(6):478-84.
Hodde et al., (2002), "Virus safety of a porcine-derived medical device: evaluation of a viral inactivation method," *Biotechnol. Bioeng.*, 79:211-216.
Hodge et al., (2006), "Costimulatory molecules as adjuvants for immunotherapy," *Front. Biosci.*, 11:788-803.
Hrouda et al, (1998), "*Mycobacterium vaccae* (SRL172): a potential immunological adjuvant elevated in rate prostate cancer," 82:870-876.
Huang et al., (2005), "A differential proteome in tumors suppressed by an adenovirus-based skin patch vaccine encoding human carcinoembryonic antigen," *Proteomics*, 5:1013-1023.
Hursting et al., (1990), "Types of dietary fat and the incidence of cancer at five sites," *Preventive Medicine*, 19:242-253.
Jaganathan et al., (2006), "Strong systemic and mucosal immune responses to surface-modified PLGA microspheres containing recombinant hepatitis B antigen administered intranasally," *Vaccine*, 24(19):4201-11.
Jager et al., (2003), "Antigen-specific immunotherapy and cancer vaccines," *Intl. J. Cancer*, 106:817-820.
Jarvinen et al., (2000), "Intranasal vaccination of New Zealand white rabbits against pasteurellosis using alginate-encapsulated *Pasteurella multocida* toxin and potassium thiocyanate extract," *Comparative Medicine*, 50:263-269.
Kende et al., (2006), "Enhancement of intranasal vaccination in mice with deglycosylated chain A ricin by LTR72, a novel mucosal adjuvant," *Vaccine*, 15;24(12):2213-21.
Kenney et al., (1999), "Protective immunity using recombinant human IL-12 and alum as adjuvants in a primate model of cutaneous leishmaniasis," J Immunol., 163(8):4481-8.
Kenney et al., (2004), "Induction of protective immunity against lethal anthrax challenge with a patch," *J. Infect. Disease*, 190:774-782.
Knoll, (2001), "Use of porcine small intestinal submucosal graft in the surgical management of personae's disease," *Urology*, 57:753-757.
Knoll, (2002), "Use of porcine small intestinal submucosal graft in the surgical management of tunical deficiencies with penile prosthetic surgery," *Urology*, 59:758-761.
Kochenderfer et al., (2007), "Maximizing CD8+ T cell responses elicited by peptide vaccines containing CpG oligodeoxynucleotides," *Clin. Immunol.*, 124:119-130.
Koller et al., (2002), "Induction of antibodies against murine full-length prion protein in wild-type mice," *J Neuroimmunol.*, 132(1-2):113-6.
Komenaka et al., (2004), "Immunotherapy for melanoma," *Clinics in Dermatology*, 22:251-265.
Langermans et al., (2005), "Effect of adjuvant on reactogenicity and long-term immunogenicity of the malaria Vaccine ICC-1132 in macaques," *Vaccine*, 23(41):4935-43.
Lantz et al., (1990), "Small intestinal submucosa as a small-diameter arterial graft in the dog," *J. Invest. Surg.*, 3:217-227.
Lantz et al., (1993), "Small intestinal submucosa as a vascular graft: a review," *J. Invest. Surg.*, 6:297-310.
Lee et al., (1999), "Increased vaccine-specific T cell frequency after peptide-based vaccination correlates with increased susceptibility to in vitro stimulation but does not lead to tumor regression," *J. Immunol.*, 163:6292-6300.
Levesque et al., (2006), "Association between immunogenicity and adsorption of a recombinant *Streptococcus pneumoniae* vaccine antigen by an aluminum adjuvant," *Hum Vaccin.*, 2(2):74-7.
Lindblad, (2004), "Aluminium compound for use in vaccines," *Immunol. Cell Biol.*, 82:497-505.
Lord et al., (2007), "Low dose metronomic oral cyclophosphamide for hormone resistant prostate cancer: a phase II study," *J. Urology*, 177:2136-2140.
Lubaroff et al., (2006), "Decreased cytotoxic T cell activity generated by co-administration of PSA vaccine and CpG ODN is associated with increased tumor protection in a mouse model of prostate cancer," *Vaccine*, 24:6155-6162.
Mantovani et al., (2003), "Reconstructive Urethroplasty using porcine acellular matrix," *Eur. Urol.*, 44:600-602.
Martin, (1997), "Development of an adjuvant to enhance the immune response to influenza vaccine in the elderly," *Biologicals*, 25(2):209-131.
Matrisian et al., (2001), "Epithelial-stromal interactions and tumor progression: meeting summary and future directions," *Cancer Res.*, 61:3844-3846.
McDevitt et al., (2003), "Transforming growth factor-B1 in a sterilized tissue derived from the pig small intestine submucosa," *J. Biomed. Mater. Res.*, 67A:637-640.
Mendez et al., (2003), "Coinjection with CpG-containing immunostimulatory oligodeoxynucleotides reduces the pathogenicity of a live vaccine against cutaneous Leishmaniasis but maintains its potency and durability," *Infect Immun.* 71(9):5121-9.
Miller et al., (2006), "The role of melatonin in immuno-enhancement: potential application in cancer," *Int. J. Exp. Path.*, 87:81-87.
Moschella et al., (2003), "Shifting gene expression profiles during ex vivo culture of renal tumor cells: implications for cancer immunotherapy," *Oncology Res.*, 14:133-145.
Mosolitis et al., (2005), "Towards therapeutic vaccines for colorectal carcinoma: a review of clinical trials," *Expert Rev. Vaccines*, 4:329-350.
Mullen et al., (2006), "Enhancement of functional antibody responses to AMA1-C1/Alhydrogel, a Plasmodium falciparum malaria vaccine, with CpG oligodeoxynucleotide," *Vaccine*, 24(14):2497-505.

(56) References Cited

OTHER PUBLICATIONS

Nomura et al., (2000), "Serum selenium and subsequence risk of prostate cancer," *Cancer Epidemiology, Biomarkers & Prevention*, 9:883-887.
Ochsenbein et al., (1999), "Immune surveillance against a solid tumor fails because of immunological ignorance," *Proc. Natl. Acad. Sci. USA*, 96:2233-2238.
O'Connor et al., (2001), "Successful repair of uretero-neobladder structure using porcine small intestine submucosa," *J. Urology*, 165:1995.
O'Connor et al., (2002), "Distal ureteral replacement with tubularized porcine small intestine submucosa," *Urology*, 60:697x-697xii.
O'Connor et al., (2002), "Novel modification of partial nephrectomy technique using porcine small intestine submucosa," *Urology*, 60:906-909.
Ohashi et al., (2000), "Significance of tumor associate eosinophilia and other inflammatory cell infiltrate in early esophageal squamous cell carcinoma," *Anticancer Res.*, 20:3025-3030.
Okaji et al., (2004), "Vaccination with autologous endothelium inhibits angiogenesis and metastasis of colon cancer through autoimmunity," *Cancer Science*, 95:85-90.
Ou et al., (2008), "Enhancement of dendritic cell-tumor fusion vaccine potency by indoleamine-pyrrole 2,3-dioxygenase inhibitor, 1-MT," *J. Cancer Res. Clin Oncol.*, 134:525-533.
Paradiso et al., (2003), "Plaque surgery for Peyronie's disease: heterologous grafts," *Archivio Italiano di Urologia e Andrologia*, 75:116-118 (Italian language with English abstract).
Peng et al., (2006), "Novel vaccines for the treatment of chronic HBV infection based on mycobacterial heat shock protein 70," Vaccin, 24(7):887-96.
Peretz et al., (2001), "Antibodies inhibit prion propagation and clear cell cultures of prion infectivity," *Nature*, 412(6848):739-43.
Peters et al., (1979), "Preparation of immunotherapeutic autologous tumor cell vaccines from solid tumors," *Cancer Res.*, 39:1353-1360.
Petrik et al., (2007), "Aluminum adjuvant linked to Gulf War illness induces motor neuron death in mice," *Neuromolecular Med.*, 9:83-100.
Petrovsky, (2006), "Novel human polysaccharide adjuvants with dual Th1 and Th2 potentiating activity," *Vaccine*, 24S2:S2/26-S2/29.
Pilla et al., (2006), "A phase II trial of vaccination with autologous, tumor-derived heat-shocked protein peptide complexes Gp96, in combination with GM-CSF and interferon-a in metastatic melanoma patients," *Cancer Immunol. Immunother.*, 55:958-968.
Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," *Infect Immun.*, 74(8):4939-44.
Pollard et al., (1986), "Production of autochthonous prostate cancer in Lobund-Wistar rats by treatments with N-Nitroso-N-methylurea and testosterone," *J. Natl. Cancer Inst.*, 77:583-587.
Pollard et al., (1987), "Autochthonous prostate cancer in Lobund-Wistar rats; a model system," *The Prostate*, 11:219-227.
Pollard et al., (2005), "Hormone-refractory prostate cancer in the Lobund-Wister rat," *Exp. Biol. Med.*, 230:520-526.
Pollard, (1998), "Lobund-Wistar rat model of prostate cancer in man," *The Prostate*, 37:1-4.
Polymenidou et al., (2004), "Humoral immune response to native eukaryotic prion protein correlates with anti-prion protection," *Proc Natl Acad Sci U S A*,101 Suppl 2:14670-6.
Qin et al., (2004), "CpG ODN enhances immunization effects of hepatitis B vaccine in aged mice," Cell Mol Immunol., 1(2):148-52.
Rechsteiner et al., (2005), "Cutting edge: priming of CTL by transcutaneous peptide immunization with imiquimod," *J. Immunol.*, 174:2476-2480.
Redfern et al., (2006), "Phase II trial of idiotype vaccination in previously treated patients with indolent non-Hodgkin's lymphoma resulting in durable clinical responses," *J. Clin. Oncol.*, 24:3107-3112.
Ringler et al., (1985), "Protection of rabbits against experimental pasteurellosis by vaccination with a potassium thiocyanate extract of *Pasteurella multocida*," *Infection & Immunity*, 49:498-504.
Rosado-Vallado et al., (2005), "Aluminium phosphate potentiates the efficacy of DNA vaccines against Leishmania mexicana," *Vaccine*, 23(46-47):5372-9.
Rosset et al., (2004), "Breaking immune tolerance to the prion protein using prion protein peptides plus oligodeoxynucleotide-CpG in mice," *J Immunol.*, 172(9):5168-74.
Rousseau et al., (2006), "Immunotherapy of high-risk acute leukemia with a recipient (autologous) vaccine expressing transgenic human CD40L and IL-2 after chemotherapy and allogeneic stem cell transplantation," *Blood*, 107:1332-1341.
Ruozi et al., (2007), "Intact collagen and atelocollagen sponges: Characterization and ESEM observation," *Mat. Sci. Eng.*, 27:802-810.
Sabirov et al., (2006), "Intranasal vaccination of neonatal mice with polysaccharide conjugate vaccine for protection against pneumococcal otitis media," *Vaccine*, 24(27-28):5584-92.
Sanderson et al., (1974), "The induction of tumour immunity in mice using glutaraldehyde-treated tumor cells," *Nature*, 248:690-691.
Schultz et al., (2002), "Porcine small intestine submucosa as a treatment for enterocutaneous fistulas," *J. Am. Coll. Surg.*, 194:541-543.
Schwarz et al., (2004), "Immunisation with a synthetic prion protein-derived peptide prolongs survival times of mice orally exposed to the scrapie agent," *Neurosci Lett.*, 350(3):187-9.
Segura-Velázquez et al., (2006), "A novel synthetic adjuvant effectively enhances the immunogenicity of the influenza vaccine," *Vaccine*, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," *Infect Immun.*, 74(4):2177-86.
Shekhar et al., (2001), "Breast stroma plays a dominant regulatory role in breast epithelial growth and differentiation: implications for tumor development and progression," *Cancer Res.*, 61:1320-1326.
Sigurdsson et al., (2002), "Immunization delays the onset of prion disease in mice," *Am J Pathol.*, 161(1):13-7.
Simons et al., (2006), "Granulocyte-macrophage colony-stimulating factor—transduced allogeneic cancer cellular immunotherapy: the GVAX® vaccine for prostate cancer," *Urol. Oncol.*, 24:419-424.
Singh et al., (1992), "Stroma is critical for preventing or permitting immunological destruction of antigenic cancer cells," *J. Exp. Med.*, 175:139-146.
Skountzou et al., (2006), "Transcutaneous immunization with inactivated influenza virus induces protective immune responses," *Vaccine*, 24:6110-6119.
Souan et al., (2001), "Modulation of proteinase-K resistant prion protein by prion peptide immunization," *Eur J Immunol.*, 31(8):2338-46.
Srinivasan et al., (2004), "Tumor antigens for cancer immunotherapy: therapeutic potential of xenogeneic DNA vaccines," *J. Translational Med.*, 2:1-12.
Stewart et al., (2006), "Pre-clinical evaluation of new adjuvant formulations to improve the immunogenicity of the malaria vaccine RTS,S/AS02A," *Vaccine*, 24(42-43):6483-92.
Suckow et al., (1991), "Heat-labile toxin-producing isolates of *Pasteurella multocida* from rabbits," *Lab. Animal Sci.*, 41:151-156.
Suckow et al., (1999), "Enhanced bone regeneration using porcine small intestinal submucosa," *J. Invest. Surg.*, 12:277-287.
Suckow et al., (2005), "Use of porcine renal capsule matrix as a full-thickness dermal wound-healing material in rats," *J. Wound Care*, 14:137-140.
Suckow et al., (2007), "Prevention of human PC-346C prostate cancer growth in mice by xenogeneic tissue vaccine," *Cancer Immunol. Immunother.*, 56:1275-1283.
Suckow et al., (2007), "Surgical Repair of Experimental Achilles Tenotomy with Porcine renal capsule material in a rat model," *J. Mater. Sci. Mater. Med.*, 18:1105-1110.
Suckow et al., (2007), "Tissue vaccines for cancer," *Expert. Rev. Vacc.*, 6:925-937.

(56) References Cited

OTHER PUBLICATIONS

Suckow et al., (2008), "Use of an extracellular matrix material as a vaccine carrier and adjuvant," *Anticancer Res.*, 28(5A):2529-2534.
Sugai et al., (2005), "A CpG-containing oligodeoxynucleotide as an efficient adjuvant counterbalancing the Th1/Th2 immune response in diphtheria-tetanus-pertussis vaccine," *Vaccine*, 23(46-47):5450-6.
Sung et al., (2006), "HBV-ISS (Dynavax)," *Curr Opin Mol Ther.*, 8(2):150-5.
Tatenhorst et al., (2005), "Genes associates with fast glioma cell migration in vitro and in vivo," *Brain Pathol.*, 15:46-54.
Teir et al., (1957), "Effects of intraperitoneally injected suspension of roetgen irradiated and non-irradiated tumor tissue on the growth of homologous tissue," *Acta Pathol. Microbiol. Scand.*, 40:273-282.
Theeten et al., (2005), "Effects of lowering the aluminium content of a dTpa vaccine on its immunogenicity and reactogenicity when given as a booster to adolescents," *Vaccine*, 10;23(12):1515-21.
Tjoa et al., (1999), "Follow-up evaluation of a phase II prostate cancer vaccine trial," *The Prostate*, 40:125-129.
Tjoa et al., (2000), "Development of a dendritic cell-based prostate cancer vaccine," *Immunology Letters*, 74:873-893.
Totterman et al., (2005), "The immunotherapy of prostate and bladder cancer," *B.J.U. Intl.*, 96:728-735.
Vitetta et al., (2006), "A pilot clinical trial of a recombinant ricin vaccine in normal humans," *Proc Natl Acad Sci U S A*, 103(7):2268-73.
Voytik-Harbin et al., (1998), "Small intestinal submucosa: a tissue-derived extracellular matrix that promotes tissue-specific growth and differentiation of cells in vitro," 4:157-174.
Wang et al., (1993), Lack of HLA class I antigen expression by melanoma cells SK-Mel-33 caused by reading a frameshift in β2-Microglobulin Messenger RHNA,: *J. Clin. Invest.*, 91:648-692.
Wei et al., (2002), "Immunotherapy of tumors with vaccines based on xenogeneic homologous molecules," *Anti-Cancer Drugs*, 13:229-235.
Wei et al., (2006), "Dendritoma vaccination combined with low dose interleukin-2 in metastatic melanoma patients induced immunological and clinical responses," *Intl. J. Oncol.*, 28:585-593.
Weiser et al., (2003), "Single layered small intestinal submucosa in the repair of sever chordee and complicated hypospadias," *J. Urology*, 170:1593-1595.
International Search Report; International Preliminary Exam Report and Written Opinion of the International Searching Authority, Mailed Jul. 22, 2009, in PCT/US09/35062.
Abraham, et al. (2000) J. Biomed. Mater Res., 29:442-452.
Higaki, et al. (2004) Vaccine, 19:3091-3096.
Hodde, et al. (2004) J. Surg. Res., 120:189-194.
International Search Report and Written Opinion, International Application PCT/US08/51877 mailed Sep. 17, 2008.
Mark A. Suckow et al. "Inhibition of prostate cancer metastasis by administration of a tissue vaccine," Springer Science+Business Media B.V., Sep. 28, 2008, 6 pages.
Stephanie M. Doctor et al. "Is Prostate Cancer Changing? Evolving Patterns of Metastatic Castration-Resistant Prostate Cancer," Cancer, vol. 120—Issue 6, Mar. 15, 2014, pp. 833-839.
Gregory R. Pond et al. "The Prognostic Importance of Metastatic Site in Men with Metastatic Castration-resistant Prostate Cancer," European Urology 65, 2014, pp. 3-6.
Carmel J. Pezaro et al. "Visceral Disease in Castration-resistant Prostate Cancer." European Urology 65, 2014, pp. 270-273.
Mayo Clinic, Diseases and Conditions—Prostate Cancer, http://www.mayoclinic.org/diseases-conditions/prostate-cancer/expert-answers/prostate-cancer-metastasis/faq-20058270, Dec. 22, 2014.

* cited by examiner

METASTASIS INHIBITION PREPARATIONS AND METHODS

BACKGROUND OF THE INVENTION

Metastasis is a complex series of steps in which cancer cells leave the original tumor site and migrate to other parts of the body via the bloodstream or the lymphatic system. To do so, malignant cells break away from the primary tumor and attach to and degrade proteins that make up the surrounding extracellular matrix (ECM), which separates the tumor from adjoining tissue. By degrading these proteins, cancer cells are able to breach the ECM and escape. When oral cancers metastasize, they commonly travel through the lymph system to the lymph nodes in the neck. The body resists metastasis by a variety of mechanisms through the actions of a class of proteins known as metastasis suppressors of which about a dozen are known.

Cancer researchers studying the conditions necessary for cancer metastasis have discovered that one of the critical events required is the growth of a new network of blood vessels, called tumor angiogenesis. Angiogenesis inhibitors have therefore been proposed in preventing the growth of metastases.

Whether or not a cancer is local or has spread to other locations affects treatment and survival. If the cancer spreads to other tissues and organs, it may decrease a patient's likelihood of survival. When cancer has metastasized, it may be treated with radiosurgery, chemotheraphy, chemotheraphy, radiation therapy, biological therapy, hormone therapy, surgery, laser immunotheraphy, or a combination of these. The choice of treatment generally depends on the type of primary cancer, the size and location of the metastasis, the patient's age and general health, and the types of treatments used previously. Unfortunately, current treatment options are rarely able to cure metastatic cancer.

Cancer of the prostate may metastasize to the bones and/or to the lungs. In a similar manner, colon cancer has the tendency to metastasize to the liver. Stomach cancer often metastasizes to the ovary in women, where it is then called a Krukenberg tumor. It is difficult for cancer cells to survive outside their region of origin, so in order to metastasize they must find a location with similar characteristics.

Prostate cancer is a significant cause of morbidity and mortality among men in the Western world. In advanced cases, the disease becomes refractory to conventional treatments and death of the patient typically results from sequelae related to metastasis to sites including the bone and lungs.

Adenocarcinoma of the prostate is one of the most common malignancies. It is estimated that there are 220,000 new cases of prostate cancer will be diagnosed in the United States in 2007, and that it will cause more than 30,000 deaths during the year. In fact, prostate adenocarcinoma is the second leading cause of cancer-related mortality among men in the United States.

With prostate cancer, as with all solid tumors, it is the metastatic encroachment of the tumor on other vital function that causes the demise of the patient. Approximately 10% of patients are diagnosed initially with metastatic disease. Ultimately, 30-40% of patients with this cancer will develop metastatic disease. Once metastasis occurs, the cancer follows a relentless progression.

Invasion is a prerequisite for migration of tumor cells in connective tissue stroma and basement membranes form the major physical barriers to the migration process. Invasion of the local extracellular matrix (ECM) by tumor cells thus can be marked as the first step in metastasis. The sequential biochemical mechanism first involves cell attachment to specific components of ECM followed by a progressive cascade of proteolytic dissolution. Prostate cancers which grow to a critical size exhibit extracapsular invasion and metastasize to specific anatomical sites apparently in response to stromal cell secretory proteins which are necessary for their growth and proliferation. Invasive migration of tumor cells within the prostate gland may occur as a function of chemokinesis along anatomical paths of least resistance which include the perineural duct. Further establishment of metastasis relies upon successful penetration of the circulatory or lymphatic system, and vessel extravasation at the secondary organ which for prostate cancer is frequently bone and/or lung tissue. Nearly all of these steps, including attachment, matrix degradation and migration, can be modeled experimentally in vitro by measuring invasion of a reconstituted basement membrane (RBM) barrier in response to fibroblast-conditioned medium (FCM) used as a chemo-attractant.

Individual molecules associated with prostate cancer have been studied for their utility as vaccine antigens. For example, prostate-specific antigen (PSA), prostate-specific membrane antigen (PSMA), and prostatic acid phosphatase (PAP) have all been identified as immunogenic. PAP, as a vaccine antigen, has been shown to induce Th1 immunity in patients and conferred moderate clinical improvement. Clinical trials showed that patients vaccinated with dendritic cells loaded with recombinant PAP/granulocyte-macrophage-colony-stimulating factor (GM-CSF) protein had moderation of PSA levels and prolonged survival. Some patients having hormone-refractory prostate cancer showed moderation of PSA levels following vaccination with dendritic cells pulsed with various antigens, including PSA and PSMA. While some clinical success has been achieved with these antigens, none have resulted in long-term survival of patients Use of autologous whole cell vaccines have been examined for a variety of cancers, including melanoma, lung cancer, colon cancer, and renal tumors. Varying degrees of efficacy were reported.

A phase I clinical trial of irradiated GM-CSF-secreting autologous prostate tumor cell vaccine therapy reported that the vaccine was well tolerated by patients and induced both B-cell and T-cell immune responses against antigens associated with prostate cancer cells. However, those investigators concluded that, while promising, autologous vaccines for prostate cancer were limited by the low yield of cells recovered from tumor harvest, even after expansion in cell culture. Instead, investigators have focused on the use of preparations composed of irradiated allogeneic prostate cancer cells, these cultured cells having been engineered to secrete GM-CSF, or allogenic cells with a *Bacillus* adjuvant as a means for treatment of prostate cancer. One study reported that vaccination slowed the rise of PSA in 40% of vaccinated patients, and an increased average time to disease progression of 58 weeks, compared to historical experience of 29-30 weeks.

Despite these and other reports, a need continues to exist in the medical and clinical arts for more effective methods and compositions for inhibiting metastasis and the spread of cancer.

SUMMARY

The present invention, in a general and overall sense, provides preparations and methods of using these preparations for inhibiting and/or halting metastasis, as well as the cancer disease progression associated with metastasis. These methods and preparations may be used in both human and non-human animals. For example, the present methods and preparations may be employed in the treatment of non-human animals including companion animals, such as cats, dogs and horses. Other types of non-human animals envisioned for treatment according to the present methods include commercially important animals, including sheep, swine, cattle and others.

In some aspects, the types of metastasis that may be inhibited and/or eliminated include metastasis to the lung and/or bone (such as to the spine). It is envisioned that the present methods and preparations will also find utility in reducing and/or preventing the metastasis of tumor/cancer cells to other organs, such as, by way of example and not limitation, metastasis to ovary, liver, brain, kidney, spleen, intestines, adrenal glands, or any other tissue and/or organ or combination of tissues and/or organs. It therefore is an object of the present invention to provide methods for inhibiting or preventing metastasis.

It is another aspect of the present invention to provide preparations for inhibiting or preventing metastasis.

In accomplishing the foregoing objects, there has been provided, in accordance with one aspect of the present invention, a method for preventing or inhibiting metastasis of a cancer, for example, a cancer of epithelial cell origin, comprising the step of administering to an animal having a cancer a composition comprising a vaccine preparation as described herein. In some embodiments, the vaccine preparation may be described as comprising a tumor tissue vaccine or a conditioned extracellular matrix (ECM) vaccine.

In some embodiments, the preparation and/or composition comprises a tumor tissue preparation that has been treated so as to deactivate any proliferating malignant cells. By way of example, this may be accomplished by treating a cell suspension of a tumor tissue preparation with a deactivating process, such as a chemical or other than chemical process. By way of example, and not limitation, a chemical deactivating process may comprise treatment and/or exposure of a tissue preparation to a deactivating amount of glutaraldehdye, formalin, or any other like deactivating chemical substance. Alternatively, the tumor tissue preparation may be treated and/or exposed to a non-chemical deactivating treatment, such as to radiation. For example, a tumor tissue preparation may be exposed to a radiation dose sufficient to eliminate malignant cell activity and/or malignant cell characteristics in the tumor tissue preparation. In some embodiments, the chemical and/or non-chemical deactivating treatment may be described as rendering the tumor tissue preparation essentially free of malignant cell activity and/or malignant cell characteristics.

In some embodiments, the tissue vaccine preparation may be described as comprising a glutaraldyhyde-fixed tumor (GFT) cell vaccine. In other embodiments, the tumor tissue preparation comprises a prostate tumor tissue preparation of glutaraldyhyde-fixed prostate tumor (GFPT) cells.

In another regard, some embodiments of the present method provide a method for inhibiting and/or eliminating metastasis attendant a hormone resistant prostate cancer and/or tumor in an animal. The animal may be a human or non-human animal.

In further embodiments, the method is used in conjunction with additional treatments. In this regard, some treatments may include surgical intervention, radiation therapy, hormonal therapy, immunotherapy, chemotherapy or cryotherapy.

In accordance with another aspect of the present invention, there is provided a pharmaceutical composition for inhibiting or preventing metastasis of a cancer and/or tumor, particularly that metastasis attendant the spread of a cancer of epithelial cell origin, comprising: (i) a composition comprising a tumor tissue preparation and (ii) a carrier. The carrier may be further described as a carrier that is effective for the therapeutic administration of said composition to the animal.

In some embodiments, the metastasis inhibition preparation comprises a tumor tissue preparation.

Other objects, features and advantages of the invention will be apparent from the following detailed description. It should be understood, however, that the detailed description and the specific examples, while providing general and specific descriptions and indicating preferred embodiments of the invention, are given by way of illustration only. Various changes and modifications within the spirit and scope of the invention will become apparent to those skilled in the art from the detailed description and other aspects of the present disclosure.

DETAILED DESCRIPTION

Figure 1:
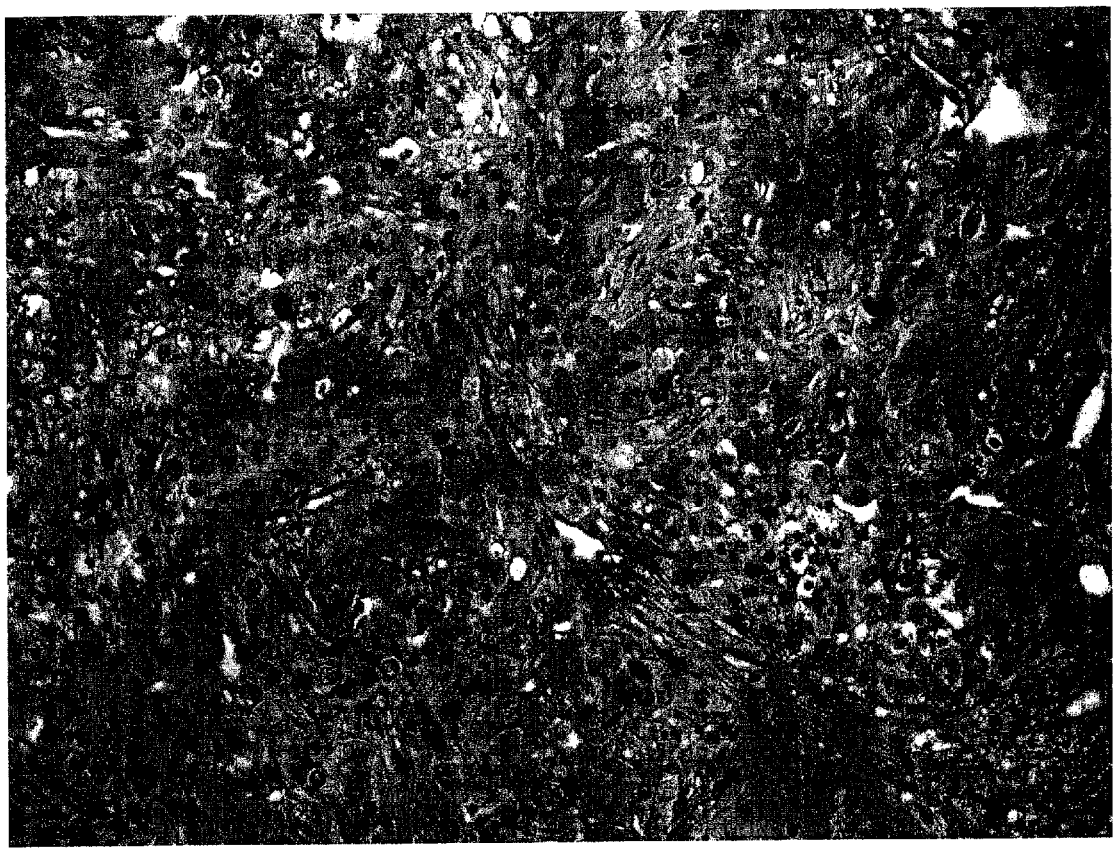
FIG. 1. Section from a prostate tumor of a non-vaccinated Lobund-Wistar rat. The tissue mass shown is a typical adenocarcinoma, with scattered acinar structures in an abundant connective tissue stroma. Section is stained with H & E, magnified ×200.

The present invention provides both preparations and/or compositions and methods of using these preparations and/or compositions for the inhibition and/or treatment of metastasis in human and non-human animals. In particular aspects, a preparation and/or composition and a method of using the preparation and/or composition as part of a method of inhibiting and/or treating metastasis attendant prostate cancer by vaccination is provided.

Among other benefits, the present preparations and/or compositions and methods are characterized by an absence of adverse side-effects relative to the experience of treatments that include chemotherapy or radiation treatment, and additional benefits as an alternative to undergoing radical prostatectomy. Moreover, with the presently disclosed methods, metastatic cancers can be targeted more specifically by use of a multivalent mixture of antigens associated with the targeted type of cancer being treated, while sparing normal adjacent tissue.

Because metastatic forms of cancer are a complex mixture of neoplastic cells, connective tissue cells, and matrix, the present multivalent vaccine captures the greatest range of relevant antigens, and therefore is of significant clinical utility. In this regard, the tissue vaccines of the present invention are made of harvested tumor material, and as such, are composed of a rich antigenic menu. In addition, the tissue vaccines provided herein are shown to be well tolerated by the animal/patient in vivo.

The whole cell vaccines described herein comprise harvested tumor material, and thereby provide a large number of different and relevant antigenic targets to the immune system, providing a highly effective multivalent vaccine preparation. These multivalent whole cell vaccines, comprising inactivated tumor tissue, are demonstrated to inhibit and/or eliminate metastasis of cancer in vivo. In particular, the present compositions prove a 70% reduction in any evidence of metastasis (such as pulmonary metastasis) in an animal having a tumor growth. This is particularly significant in that the reduced metastatic burden represents animals essentially free of metastasis. The present methods and compositions/preparations also evidence a significant reduction in the size or number of metastatic foci.

The present preparations and/or compositions and methods are demonstrated to be effective in the treatment of hormone-refractory cancers, as well as the metastasis of these cancers. For example, the present compositions and methods are effective in the treatment and/or inhibition of hormone refractory prostate cancer and metastasis of these cancers. This is significant because, among other reasons, cancers that have become hormone refractory have been historically recognized as more difficult to contain and treat. Thus, the activity of the present methods and preparations for effectively inhibiting these types of cancers reduces and/or eliminates technical challenges in available treatment options for these patients. The availability of adequate amounts of autologous tumor material does not constitute a limiting factor when considering this as a treatment option among this particular group of patients.

Tumor material harvested from other sources may also be used for preparation of the presently described whole cell vaccines. For example, a xenogeneic tissue vaccine composed of harvested subcutaneous PAIII prostate tumors (in for example, LW rats) stimulates sufficient immunity in immunocompetent animals. Specifically, Ncr-Foxn1<nu> mice splenocytes were incubated with human PC346C prostate cancer cells and administered to syngeneic nu/nu mice. Nearly 70% of the immunodeficient mice were completely free of tumor growth compared to none of the controls. While not intending to be limited to any particular mechanism of action and/or theory, this protective response may be mediated by Th1 immunity. In the present methods and compositions, immunization with the OFT cell vaccine stimulated increases in the Th-1-associated cytokines, IFN-γ and TNF-α, suggesting concordance with the earlier results in the xenogeneic system. Xenogeneic tumor tissue represents a source from which material can be harvested for construction of tissue vaccines. This approach, among others, overcomes the limitations identified by earlier investigators.

Vaccination of rats with glutaraldehdye-fixed material harvested directly from tumors completely eliminates metastasis in 70% of rats bearing autochthonous prostate tumors. Thus, the present preparations and/or compositions and methods provide a tissue vaccine having utility in the prevention and/or inhibition of metastasis of prostate cancer.

DEFINITIONS

The abbreviations and terms in the present disclosure are employed in contemplation of their fullest meaning consistent with the disclosed and claimed invention. The following brief explanations are entirely illustrative and neither exhaustively define nor limit the invention disclosed and claimed herein. The full meaning of the terms will be clear from an understanding of the invention based on contemplation of the disclosure as a whole in light of a full understanding of the pertinent arts.

METASTASIS: As set out in Hill, R. P., Chapter 11, Metastasis, pp 178-195 in The Basic Science of Oncology, Tannock et al., Eds., McGraw-Hill, New York (1992), which is incorporated by reference herein in its entirety, metastasis is "The ability of cells of a cancer to disseminate and form new foci of growth at noncontiguous sites (i.e., to form metastases)".

Similarly, metastasis is described in Aznavoorian et al., Cancer 71: 1368-1383 (1993) (incorporated by reference in its entirety) as "The transition from in situ tumor growth to metastatic disease as defined by the ability of tumor cells of the primary site to invade local tissues and to cross tissue barriers. To initiate the metastatic process, carcinoma cells must first penetrate the epithelial basement membrane and then invade the interstitial stroma. For distant metastases, intravasation requires tumor cell invasion of the subendothelial basement membrane that must also be negotiated during tumor cell extravasation. The development of malignancy is also associated with tumor-induced angiogenesis that not only allows for expansion of the primary tumor, but also permits easy access to the vascular compartment due to defects in the basement membranes of newly formed vessels."

MALIGNANT: from the Latin roots mal-="bad" and -genus="born") is a medical term used to describe a severe and progressively worsening disease. The term is most familiar as a description of cancer. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

EPITHELIAL CELL ORIGIN: derived from an epithelial cell, of a tissue.

INHIBITION: inhibition of metastasis may be measured by many parameters in accordance with the present invention and, for instance, may be assessed by delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition, is referred to herein as prevention. In addition, the inhibition of metastasis may be identified by a reduction in metastatic foci present in the animal.

PREVENTION: in relation to metastasis, virtually complete inhibition, no metastasis if it had not occurred, no further metastasis if there had already been metastasis of a cancer. See INHIBITION.

COMPOSITIONS: Any non-toxic, inert and effective carrier may be used to formulate compositions of the present invention. Well known carriers used to formulate other therapeutic compounds for administration to humans particularly will be useful in the compositions of the present invention. Pharmaceutically acceptable carriers, excipients and diluents in this regard are well known to those of skill, such as those described in the MERCK INDEX, 11th Ed., Budavari et al., Eds., Merck & Co., Inc., Rahway, N.J. (1989), which is incorporated by reference herein in its entirety. Examples of such useful pharmaceutically acceptable excipients, carriers and diluents include distilled water, physiological saline, Ringer's solution, dextrose solution, Hank's solution and DMSO, which are among those preferred for use in the present invention.

In particular, for instance Mantile et al., J. Biol Chem. 268: 20343-20351 (1993), incorporated herein by reference above, report on sterile formulations, that may also be useful in preparing the present compositions.

CANCERS: Methods and compositions of the present invention may be applied to the treatment of a variety of metastasis attendant a cancer, such as a cancer of epithelial cell origin. Among these are metastatic cancers of breast, lung, colon, bladder, prostate, gastrointestinal tract, endometrium, tracheal-bronchial tract, pancreas, liver, uterus, nasopharynges and the skin. In some aspects, the target cancer is prostate cancer of epithelial cell origin.

The following detailed discussion of prostate cancers is provided in illustration of the compositions and methods of the invention not only as to prostate cancers, but also other cancers that may be treated in analogous or identical fashion, in accordance with the present invention.

Metastatic potential of prostate cancers of epithelial cells origin can be inhibited by compositions and methods of the invention. In particular, metastasis of these cancers can be inhibited and/or eliminated by a preparation and/or composition comprising a whole tissue preparation of prostate tumor cells.

DOSE: The quantity of the whole cell vaccine for effective therapy will depend upon a variety of factors, including the type of cancer, means of administration, physiological state of the patient, other medications administered, and other factors.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of metastatic cancers in accordance with the present invention.

These considerations, as well as effective formulations and administration procedures are well known in the art and are described in standard textbooks, such as GOODMAN AND GILMAN'S: THE PHARMACOLOGICAL BASES OF THERAPEUTICS, 8th Ed., Gilman et al. Eds. Pergamon Press (1990) and REMINGTON'S PHARMACEUTICAL SCIENCES, 17th Ed., Mack Publishing Co., Easton, Pa. (1990), both of which are incorporated by reference herein in their entirety.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Example 1

Materials and Methods

The present example provides a description of the materials and some of the particular methods employed in the present invention.
Materials and Methods
Animals Male LW rats were obtained from the LW rat breeding colony at the University of Notre Dame. This line arose spontaneously from a breeding colony of germfree inbred Wistar rats. Large, autochthonous tumors arise in the prostate/seminal vesicle complex; these tumors metastasize to the lungs via the lymphatics. The rats were housed in polycarbonate cages provided with hardwood shavings. A natural ingredient diet, Teklad L-485 (Harlan Teklad, Inc., Madison, Wis.) and fresh water were provided ad libitum. All animal studies were conducted in a facility accredited by the Association for Assessment and Accreditation of Laboratory Animal Care, International; studies were approved by the University of Notre Dame Institutional Animal Care and Use Committee.
Vaccine Preparation A glutaraldehyde-fixed tumor (GFT) cell vaccine was prepared as previously described. Briefly, 3 g of a LW rat subcutaneous tumor, produced by administration of prostate adenocarcinoma (PAIII) cells which were originally isolated from an autochthonous, metastatic adenocarcinoma in a LW rat were harvested. The tissue was finely minced, and the cells separated using an 80-mesh screen to create a cell suspension in modified Eagle's medium (MEM). The cell suspension was then incubated in 2.5% glutaraldehyde (v/v) at 37° C. for 60 min and then washed thoroughly with medium. This preparation was washed three (3) times in a modified Eagles media. The washed preparation was then suspended in a weight/volume ratio of 1:1 in a Freunds complete adjuvant. The "booster" tissue vaccine preparations were prepared in a Freund's incomplete adjuvant. The overall concentration of the preparations was about 1 mg (tissue)/ml, expressed as minced cell mass per ml adjuvant.

Example 2

Tumor Metastasis Inhibition In Vivo

The present example is provided to demonstrate, among other things, the utility of the present invention for reducing and/or inhibiting tumor metastasis in an animal, and in particular, a non-human animal. The present example also demonstrates the utility of the invention as a method for inhibiting the metastasis of prostate cancer to the lung.

A group of sixty 3-4 month old, male LW rats were administered a single intravenous dose (30 mg/kg) of methylnitrosourea (MNU). At subsequent 2-month intervals, rats were anesthetized with an intramuscular dose of ketamine (90 mg/kg) and xylazine (10 mg/kg) and a silastic capsule containing 20 mg of testosterone propionate aseptically implanted into the subcutaneous space of the dorsal thorax. This method results in 70-80% of treated rats developing autochthonous, metastasizing hormone-refractory prostate tumors. These tumors developed within 8 months of MNU inoculation.

Beginning at 4 months after MNU inoculation, rats were palpated weekly for caudal intraabdominal masses indicative of prostate tumors. Based upon experience with this system, tumors may be readily detected when they reach approximately 0.5 cm in diameter. Tumor-bearing rats were randomly assigned to one of three groups: no treatment (11 rats); vaccination with MEM (10 rats); or vaccination with the GFT cell vaccine (19 rats). Animals were vaccinated initially when tumors were first palpated and weekly until the time of euthanasia; the minimum number of vaccinations was two and the maximum number was nine, with an average of 3.6 overall (3.6 for GFT cell vaccinated rats and 3.7 for MEM-vaccinated rats).

Rats were euthanized by exsanguinations under halothane anesthesia when they became clinically debilitated. Debilitation was typically the result of hydroureter and hydronephrosis resulting from the tumor mass in the caudal abdomen. Four rats in the GFT cell vaccination group were observed to have complete regression of tumors; one was euthanized and found to have a renal abscess, the others were euthanized after four, six, or nine weekly vaccinations to confirm that the tumor had regressed.

Necropsy and Histopathology

At the time of euthanasia, animals underwent necropsy. Prostate-seminal vesicle (PSV) complexes, including tumors, were weighed and fixed in 10% neutral buffered formalin for 24 hours and then placed in 70% isopropyl alcohol. Lungs were examined for the presence of any metastatic foci on pleural surface, typical of metastasis in this model. After fixation, PSV complexes were serially sectioned at 4-5 μm and stained with hematoxylin and eosin.

Splenocyte Culture and Supernatant Cytokine Production

Ten rats from groups vaccinated with either MEM or GFT cells were euthanized and single cell suspensions prepared by puncturing the splenic capsule with a thin syringe and squeezing the cells out. The single cell suspensions were washed in sterile PBS and then incubated on ice for 10 min in TRIS buffer with ammonium chloride. After two washes in RPMI 1640 medium, the cells were resuspended in culture medium and counted. Culture medium consisted of RPMI 1640 with 10% fetal calf serum, 100 U/ml penicillin, 100 μg/ml streptomycin, 50 μM 2-mercaptoethanol and 2 mM L-glutamine. To each well of sterile 24-well microplates, $3 \times 10^6$ splenocytes were added. Splenocytes were pulsed with either GFT cells ($5 \times 10^4$ GFT cells per well) or sterile RPMI medium (as a control). Cultures were incubated for 72 h in 5% $CO_2$. Supernatants from cultured splenocytes were collected and frozen at −80° C. until evaluated for cytokine production.

Concentrations of TNF-α and IFN-γ were measured by a general multiplex assay protocol in a sandwich immunoassay system employing microspheres and using the Luminex-100 (Luminex Corp., Austin, Tex.), a dual-laser flow analyzer. All cytokines were simultaneously measured from a single specimen.

Statistical Analysis

Group differences in weights of PSV complexes were evaluated for significance using the Bonferroni multiple comparisons test with significance reached when $p \leq 0.05$. Results for presence of pulmonary metastases were compared between groups using the $\chi^2$ test with two degrees of freedom. Differences were considered to be significant when $p \leq 0.05$.

Example 3

Vaccination Inhibits Pulmonary Metastasis

The present example demonstrates the utility of the present invention for preventing and/or reducing metastasis in an animal. The present example also demonstrates the utility of the method for inhibiting and/or preventing metastasis, and in particular, metastasis of a tumor of prostate origin, to another organ. For example, metastasis may be prevented from progressing to the lung.

Figure 2:
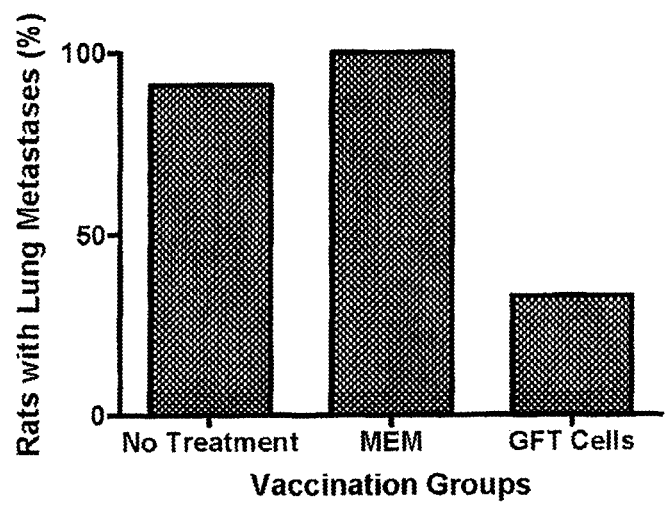
FIG. 2. Percentage of rats having pulmonary metastases from primary prostate tumor. Tumor bearing rats underwent weekly vaccination with either media (MEM) or a tissue vaccine, the tissue vaccine comprising a suspension of glutaraldehyde-fixed tumor (GFT) cells. In addition, an untreated group was included. Most untreated and (sham) MEM-vaccinated rats had evidence of pulmonary metastases. In contrast, 70% of GFT cell-vaccinated rats were completely free of metastasis in the lungs.

Vaccination with the GFT cell vaccine induces protective immunity against metastasis from autochthonous prostate cancer. To demonstrate this, non-vaccinated and MEM- and GFT cell-vaccinated rats were evaluated for the presence of metastasis in the lungs, the typical site of metastasis in the Lobund-Wistar rat model. Nearly all rats in the non-vaccinated (10/11) and the MEM-vaccinated (10/10) groups had metastatic foci in the lungs (FIG. 2). In contrast, a significant ($p \leq 0.001$) reduction in the incidence of rats having pulmonary metastasis was noted in tumor-bearing GFT cell-vaccinated rats (5/15).

Serial sections of lung lobes from rats noted to be free of grossly observable metastatic foci showed that they were also free of histologic evidence of neoplasia.

Example 4

Cell-Mediated Immune Response

The production of IFN-γ and TNF-α in supernatants of cultured splenocytes was examined in response to vaccination to demonstrate that vaccination with the whole cell tissue preparations as described herein (GFT treated) induced a Th1 response (T-cell, cell-mediated immune response). There exist several advantages to the demonstration of a cell-mediated response, rather than a humoral, or B-cell mediated response, with the whole cell preparations disclosed. In addition, the observation of this characteristic may be used to distinguish the present preparations and methods from other cancer and/or metastasis inhibiting preparations and methods.

Vaccine adjuvants such as the preparations and compositions provided here, that are specifically shown to enhance cell-mediated immunity verses humoral immunity, can be anticipated to further enhance an animal's protective immune response. Further, because cell-mediated immunity provides a variety of clinical benefits in patients, vaccination and/or treatment with the whole cell vaccine preparations provided in the present disclosure and variants thereof, yield substantial clinical advantage in the overall care and management of disease in the patient.

Figure 3A:
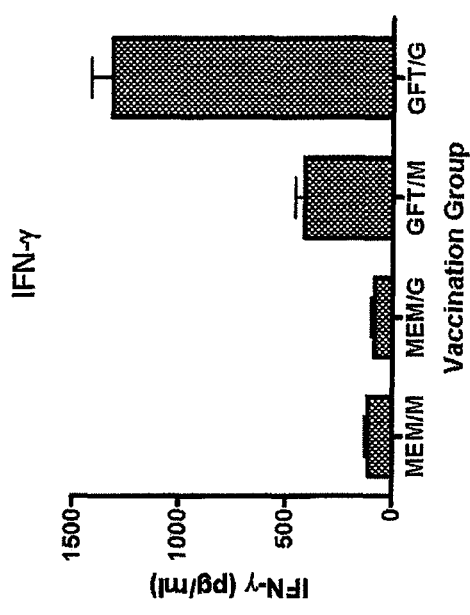
FIG. 3A-3B. IFN-γ (3A) and TNF-α (3B) levels in supernatants of cultured splenocytes from vaccinated rats. Treatment groups are vaccinated with MEM and pulsed with MEM (MEM/M); vaccinated with MEM and pulsed with GFT cells (MEM/G); vaccinated with GFT cells and pulsed with MEM (GFT/M); and vaccinated with GFT cells and pulsed with GFT cells (GFT/G). Supernatants were harvested after 72 h and cytokines measured using a general multiplex assay protocol in a sandwich immunoassay system employing microspheres and using the Luminex-100 (Luminex Corp.), a dual-laser flow analyzer. For both IFN-γ and TNF-α, the mean value for GFT/G supernatants was significantly ($P \leq 0.001$) greater than for all other groups. No other significant differences between groups were found. Values are in pg/ml.
Figure 3B:
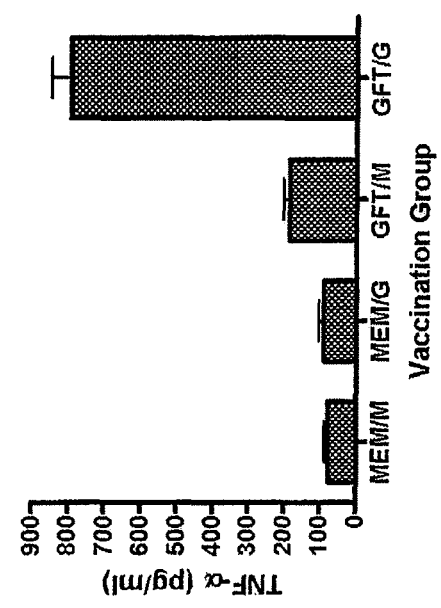

FIG. 3 summarizes the cytokine content of supernatants from cultured splenocytes of rats from all treatment groups. Compared to media-treated controls, rats immunized with the GFT cell vaccine had significantly increased ($P \leq 0.001$) levels of IFN-γ and TNF-α, cytokines associated with a Th1 immune response. Further, splenocytes from rats vaccinated with the GFT cells had significantly increased ($P \leq 0.001$) levels of both cytokines when pulsed with GFT cells versus media.

BIBLIOGRAPHY

The following references are specifically incorporated herein by reference in their entirety.

1. Edwards B K, Brown M L, Wingo P A, Howe H L, Ward E, Ries L A, Schrag D, Jamison P M, Jemal A, Wu X C, Friedman C, Harlan L, Warren J, Anderson R N, Pickle L W (2005) Annual report to the nation on the status of cancer, 1975-2002, featuring population-based trends in cancer treatment. J Natl Cancer Inst 97:1407-1427.
2. Moody D B, Robinson J C, Ewing C M, Lazenby A J, Isaacs W B (1994) Interleukin-2 transfected prostate cancer cells generate a local antitumor effect in vivo. Prostate 24:244-251.
3. Vieweg J, Rosenthal F M, Bannerji R, Heston W D, Fair W R, Gansbacher B, Gilboa E (1994) Immunotherapy of prostate cancer in the Dunning rat model: use of cytokine gene modified tumor vaccines. Cancer Res 54:1760-1765.
4. Granziero L, Krajewski S, Famess P, Yuan L, Courtney M K, Jackson M R, Peterson P A, Vitiello A (1999) Adoptive immunotherapy prevents prostate cancer in a transgenic animal model. Eur J Immunol 29:1127-1138.

5. Hrouda D, Todryk S M, Perry M J, Souberbielle B E, Kayaga J, Kirby R S, Dalgleish A G (2000) Allogeneic whole-tumour cell vaccination in the rat model of prostate cancer. BJU Int 86:742-748.
6. Zhang S, Zeng G, Wilkes D S, Reed G E, McGarry R C, Eble J N, Cheng L (2003) Dendritic cells transfected with interleukin-12 and pulsed with tumor extract inhibit growth of murine prostatic carcinoma in vivo. Prostate 55:292-298.
7. Suckow M A, Wolter W R, Pollard M (2005) Prevention of de novo prostate cancer by immunization with tumor-derived vaccines. Cancer Immunol Immunother 54:571-576.
8. Pollard M, Suckow M A (2006) Dietary prevention of hormone refractory prostate cancer in Lobund Wistar rats: a review of studies in a relevant animal model. Comp Med 56:461-467.
9. Pollard M, Luckert P H (1975) Transplantable, metastasizing adenocarcinomas in rats. J Natl Cancer Inst 54:643-649.
10. Corman J M, Secarz E E, Nanda N K (1998) Recognition of prostate-specific antigenic peptide determinants by human CD4 and CD8 T cells. Clin Exp Immunol 114:166-172.
11. Correale P, Walnsley K, Nieroda C, Zaremba S, Zhu M, Schlom J, Tsang K Y (1997) In vitro generation of human cytotoxic T lymphocytes specific for peptides derived from prostate-specific antigen. J Natl Cancer Inst USA 89:293-300.
12. Xue B H, Zhang Y, Sosman J A, Peace D J (1997) Induction of human cytotoxic T lymphocytes specific for prostate-specific antigen. Prostate 30:73-78.
13. Matsueda S, Takedatsu H, Yao A, Tanaka M, Noguchi M, Itoh K, Harada M (2005) Identification of peptide vaccine candidates for prostate cancer patients with HLS-A3 super-type alleles. Clin Cancer Res 11:6933-6943.
14. Harada M, Kobayashi K, Matsueda S, Nakagawa M, Noguchi M, Itoh K (2003) Prostate-specific antigen-derived epitopes capable of inducing cellular and humoral responses in HLA-A24+ prostate cancer patients. Prostate 57:152-159.
15. Lu J, Celis E (2002) Recognition of prostate tumor cells by cytotoxic T lymphocytes specific for prostate-specific membrane antigen. Cancer Res 62:5807-5812.
16. Horiguchi Y, Nukaya I, Okazawa K, Kawashima I, Fikes J, Sette A, Tachibana A, Takesako K, Murai M (2002) Screening of HLA-A24-restricted epitope peptides from prostate-specific membrane antigen that induces specific antitumor cytotoxic T lymphocytes. Clin Cancer Res 8:3885-3892.
17. Kobayashi H, Omiya R, Sodey B, Yanai M, Oikawa K, Sato K, Kimura S, Senju S, Nishimura Y, Tateno M, Celis E (2003) Identification of naturally processed helper T-cell epitopes from prostate-specific membrane antigen using peptide-based in vitro stimulation. Clin Cancer Res 9:5386-5393.
18. McNeel D G, Nguyen L D, Disis M L (2001) Identification of T helper epitopes from prostatic acid phosphatase. Cancer Res 61:5161-5167.
19. Small E J, Fratesi P, Reese D M, Strang G, Laus R, Peshwa M V, Valone F H (2000) Immunotherapy of hormone-refractory prostate cancer with antigen-loaded dendritic cells. J Clin Oncol 18:3894-3903.
20. Fong L, Brockstedt D, Benike C, Breen J K, Strang G, Ruegg C L, Engleman E G (2001) Dendritic cell-based xenoantigen vaccination for prostate cancer immunotherapy. J Immunol 167:7150-7156.
21. Burch P A, Breen J K, Buckner J C, Gastineau D A, Kaur J A, Laus R L, Padley D J, Peshwa M V, Pitot H C, Richardson R L, Smits B J, Sopapan P, Strang G, Valone F H, Vuk-Pavlovic S (2000) Priming tissue-specific cellular immunity in a phase I trial of autologous dendritic cells for prostate cancer. Clin Cancer Res 6:2175-2182.
22. Small E J, Schellhammer P F, Higano C S, Neumanaitis J, Valone F, Hershberg R (2005) Results of a placebo-controlled phase III trial of immunotherapy with APC8015 for patients with hormone refractory prostate cancer (HRPC). Proc Am Soc Clin Oncol 23(16S):4500.
23. Burch P A, Croghan G A, Gastineau D A, Jones L A, Kaur J S, Kylstra J W, Richardson R L, Valone F H, Vuk-Pavlovic S (2004) Immunotherapy (APC8015, Provenge) targeting prostatic acid phosphatase can induce durable remission of metastatic androgen-independent prostate cancer: a Phase 2 trial. Prostate 60:197-204.
24. Fuessel S, Meye A, Schmitz M, Zastrow S, Linné C, Richter K, Löbel B, Hakenberg O W, Hoelig K, Rieber E P, Wirth M P (2006) Vaccination with hormone-refractory prostate cancer patients with peptide cocktail-loaded dendritic cells: results of a phase I clinical trial. Prostate 66:811-821.
25. Dillman R O, Nayak S K, Barth N M, DeLeon C, Schwartzberg L S, Spitler L E, Church C, O'Connor A A, Beutel L D (1998) Clinical experience with autologous tumor cell lines for patient-specific vaccine therapy in metastatic melanoma. Cancer Biother Radiopharm 13:165-173.
26. Baars A, Claessen A M E, van den Eertwegh A J M, Gall H E, Stam A G M, Meijer S, Giaccone G, Meijer C J L M, Scheper R J, Wagstaff J, Vermorken J B, Pinedo H M (2000) Skin tests predict survival after autologous tumor cell vaccination in metastatic melanoma: experience in 81 patients. Ann Oncol 11:965-970.
27. Berd D, Maguire H C, Jr, McCue P, Mastrangelo M J (1990) Treatment of metastatic melanoma with an autologous tumor-cell vaccine: clinical and immunologic results in 64 patients. J Clin Oncol 8:1858-1867.
28. Stack B H, McSwan N, Stirling J M, Hole D J, Spilg W G, McHattie I, Elliott J A, Gillis C R, Turner M A, White R G (1982) Autologous x-irradiated tumour cells and percutaneous BCG in operable lung cancer, Thorax 37:588-593.
29. Vermorken J B, Claessen A M E, van Tinteren H, Gall H E, Ezinga R, Meijer S, Scheper R J, Meijer C J L M, Bloemena E, Ransom J H, Hanna M G, Jr, Pinedo H M (1999) Active specific immunotherapy for stage II and stage III human colon cancer: a randomized trial. Lancet 353:345-350.
30. Jocham D, Richter A, Hoffinann L, Iwig K, Fahlenkamp D, Zakrzewski G, Schmitt E, Danneberg T, Lehmacher W, von Wietersheim J, Doehn C (2004) Adjuvant autologous renal tumour cell vaccine and risk of tumour progression in patients with renal-cell carincoma after radical nephrectomy: phase III, randomised controlled trial. Lancet 363:594-599.
31. Simons J W, Mikhak B, Chang J-F, DeMarzo A M, Carducci M A, Lim M, Weber C E, Baccala A A, Goemann M A, Clift S M, Ando D G, Levitsky H I, Cohen L K, Sanda M G, Mulligan R C, Partin A W, Carter H B, Piantadosi S, Marshall F F, Nelson W G (1999) Induction of immunity to prostate cancer antigens: results of a clinical trial of vaccination with irradiated autologous prostate tumor cells engineered to secrete granulocyte-macrophage colony-stimulating factor using ex vivo gene transfer. Cancer Res 59:5160-5168.

32. Simons J W, Mikhak B, Chang J F, DeMarzo A M, Carducci M A, Lim M, Weber C E, Baccala A A, Goemann M A, Clift S M, Ando D G, Levitsky H I, Cohen L K, Sanda M G, Mulligan R C, Partin A W, Carter H B, Piantadosi S, Marshall F F, Nelson W G (1999) Induction of immunity to prostate cancer antigens: results of a clinical trial of vaccination with irradiated autologous prostate tumor cells engineered to secrete granulocyte-macrophage colony-stimulating factor using ex vivo gene transfer. Cancer Res 59:5160-5168.

33. Simons J, Nelson W, Nemunaitis J, Centeno A, Dula E, Urba W, Smith D, Marshall F, Howard C, Ando D, Small E (2002) Phase II trials of a GM-CSF gene-transduced prostate cancer cell line vaccine (GVAX) in hormone refractory prostate cancer. Proc Am Soc Clin Oncol 21:729.

34. Michael A, Ball G, Quatan N, Wushishi F, Russell N, Whelan J, Chakraborty P, Leader D, Whelan M, Pandha H (2005) Delayed disease progression after allogeneic cell vaccination in hormone-resistant prostate cancer and correlation with immunologic variables. Clin Cancer Res 11:4469-4478.

The invention is claimed as follows:

1. A method for inhibiting prostate tumor metastasis in an animal comprising:
   administering to an animal having a metastatic prostate tumor a composition comprising a prostate tumor cell preparation; and
   inhibiting prostate tumor metastasis to the lung,
wherein said prostate tumor cell preparation is inactivated with a chemically deactivating substance comprising glutaraldehyde and is non-malignant and comprises tumor tissue cells and tumor connective tissue stroma.

2. The method of claim 1 wherein the prostate tumor cell preparation is an inactivated prostate tumor preparation.

3. The method of claim 1 wherein the animal is a non-human animal.

4. The method of claim 1 wherein the animal is a human.

5. The method of claim 1 wherein the prostate tumor cell preparation is prepared by a method comprising the steps of
   mincing a volume of prostate tumor tissue and tumor stromal tissue to provide a minced cell preparation;
   processing said minced cell preparation so as to provide a suspension of prostate tumor cells; and
   inactivating said suspension of prostate tumor cells with a chemical treatment so as to provide a non-malignant prostate tumor cell preparation.

6. The method of claim 5 wherein a suspension of the minced cell preparation is provided by screening the minced cell preparation through an 80-mesh screen.

7. The method of claim 1 wherein the metastatic tumor is a autochthonous, metastasizing hormone-refractory prostate tumor.

8. The method of claim 1 wherein the inhibition of metastasis to the lung is evidenced by the absence of metastatic foci on a pleural lung surface of an animal.

9. A method for inhibiting pulmonary metastasis of a prostate cancer in an animal comprising:
   administering to an animal having prostate cancer a composition comprising a prostate tumor cell preparation; and
   inhibiting pulmonary metastasis of the cancer in the treated animal,
wherein said prostate tumor cell preparation is chemically treated with a preparation comprising glutaraldehyde.

* * * * *